(12) United States Patent
Hakansson et al.

(10) Patent No.: US 8,449,620 B2
(45) Date of Patent: May 28, 2013

(54) ARTIFICIAL JOINT

(75) Inventors: Hakan Hakansson, Lund (SE); Eva Stahl Wernersson, Lund (SE); Johan Ferner, Malmo (SE)

(73) Assignee: GS Development AB (SE)

( * ) Notice: Subject to any disclaimer, the term of this patent is extended or adjusted under 35 U.S.C. 154(b) by 259 days.

(21) Appl. No.: 12/742,088

(22) PCT Filed: Nov. 5, 2008

(86) PCT No.: PCT/EP2008/065016
§ 371 (c)(1),
(2), (4) Date: May 7, 2010

(87) PCT Pub. No.: WO2009/060006
PCT Pub. Date: May 14, 2009

(65) Prior Publication Data
US 2010/0256770 A1 Oct. 7, 2010

(30) Foreign Application Priority Data
Nov. 7, 2007 (EP) .................................... 07120198

(51) Int. Cl.
*A61F 2/42* (2006.01)
(52) U.S. Cl.
CPC .................................. *A61F 2/4241* (2013.01)
USPC .................................................... 623/22.16
(58) Field of Classification Search
CPC ................................................... A61F 2/4241
USPC .......... 623/21.11–21.19, 19.11–19.14, 20.11, 623/20.12, 17.14, 20.22, 22.15, 23.4; 403/38, 403/68, 59, 90, 76, 72, 114, 150, 151, 152, 403/164, 202, 53–57, 74
See application file for complete search history.

(56) References Cited

U.S. PATENT DOCUMENTS
751,273 A * 2/1904 Fahrney et al. ............. 285/127.2
771,637 A * 10/1904 Hoffmann ..................... 464/128
(Continued)

FOREIGN PATENT DOCUMENTS
DE 2814752 A1 10/1978
DE 19628476 A1 1/1997
(Continued)

OTHER PUBLICATIONS
International Search Report for PCT/EP2008/065016, Dated Jan. 14, 2009.

*Primary Examiner* — Alvin Stewart
(74) *Attorney, Agent, or Firm* — Thomas A. Runk; Fulwider Patton LLP

(57) ABSTRACT

An artificial joint for implantation in humans and animals, the joint comprising a joint body arranged between two base elements which are adapted to be connected to adjoining bone parts. The two base elements comprise horizontal and vertical retaining members respectively, that hold the joint body between them. The joint body comprises curved surfaces arranged to make sliding contact to corresponding curved surfaces of at least one base element. The joint body this way distributes the applied forces over a large surface to withstand the load initiated by the patient. The joint body is kept in position using pins held by retaining members at the base elements. The angle of motion can be predetermined by the design of the implant body to mimic the movement of a normal finger.

18 Claims, 3 Drawing Sheets

U.S. PATENT DOCUMENTS

| | | | |
|---|---|---|---|
| 3,377,088 A * | 4/1968 | Millay et al. | 403/57 |
| 3,506,982 A * | 4/1970 | Steffee | 623/21.16 |
| 3,638,243 A * | 2/1972 | Campbell et al. | 623/20.22 |
| 3,708,805 A * | 1/1973 | Scales et al. | 623/20.12 |
| 3,765,033 A * | 10/1973 | Goldberg et al. | 623/20.26 |
| 3,795,922 A * | 3/1974 | Herbert et al. | 623/20.22 |
| 3,837,008 A * | 9/1974 | Bahler et al. | 623/21.13 |
| 3,868,730 A * | 3/1975 | Kaufer et al. | 623/20.22 |
| 3,869,729 A * | 3/1975 | Attenborough | 623/20.25 |
| 3,869,730 A | 3/1975 | Skobel | |
| 3,916,451 A * | 11/1975 | Buechel et al. | 623/23.4 |
| 3,990,118 A * | 11/1976 | Strickland et al. | 623/23.39 |
| 4,003,096 A * | 1/1977 | Frey | 623/21.13 |
| 4,040,130 A * | 8/1977 | Laure | 623/21.13 |
| 4,040,131 A * | 8/1977 | Gristina | 623/19.12 |
| 4,059,854 A * | 11/1977 | Laure | 623/21.16 |
| 4,079,469 A * | 3/1978 | Wadsworth | 623/20.12 |
| 4,106,128 A * | 8/1978 | Greenwald et al. | 623/21.13 |
| 4,134,158 A * | 1/1979 | Laure | 623/20.24 |
| 4,180,871 A * | 1/1980 | Hamas | 623/21.13 |
| 4,193,139 A * | 3/1980 | Walker | 623/21.17 |
| 4,213,208 A * | 7/1980 | Marne | 623/21.16 |
| 4,276,660 A * | 7/1981 | Laure | 623/21.16 |
| 4,304,011 A * | 12/1981 | Whelan, III | 623/21.16 |
| 4,307,473 A * | 12/1981 | Weber | 623/21.12 |
| 4,352,212 A * | 10/1982 | Greene et al. | 623/21.16 |
| 4,383,337 A * | 5/1983 | Volz et al. | 623/20.12 |
| 4,473,240 A * | 9/1984 | Sanada | 280/771 |
| 4,714,476 A * | 12/1987 | Ranawat et al. | 623/21.12 |
| 4,725,280 A * | 2/1988 | Laure | 623/21.16 |
| 5,047,059 A * | 9/1991 | Saffar | 623/21.15 |
| 5,133,761 A * | 7/1992 | Krouskop | 623/21.16 |
| 5,147,386 A * | 9/1992 | Carignan et al. | 623/21.16 |
| 5,290,314 A * | 3/1994 | Koch et al. | 623/21.16 |
| 5,314,485 A * | 5/1994 | Judet | 623/21.13 |
| 5,401,269 A * | 3/1995 | Buttner-Janz et al. | 623/17.15 |
| 5,405,400 A * | 4/1995 | Linscheid et al. | 623/21.15 |
| 5,405,401 A * | 4/1995 | Lippincott et al. | 623/21.15 |
| 5,458,647 A * | 10/1995 | Brochier et al. | 623/21.17 |
| 5,549,681 A * | 8/1996 | Segmuller et al. | 623/23.4 |
| 5,674,296 A * | 10/1997 | Bryan et al. | 623/17.16 |
| 5,674,297 A * | 10/1997 | Lane et al. | 623/21.16 |
| 5,702,457 A * | 12/1997 | Walch et al. | 623/19.13 |
| 5,702,471 A * | 12/1997 | Grundei et al. | 623/21.16 |
| 5,723,018 A * | 3/1998 | Cyprien et al. | 623/19.13 |
| 5,776,202 A * | 7/1998 | Copf et al. | 623/18.11 |
| 5,938,700 A * | 8/1999 | Lippincott, III | 623/21.15 |
| 6,027,534 A * | 2/2000 | Wack et al. | 623/20.12 |
| 6,051,751 A * | 4/2000 | Sioshansi et al. | 128/898 |
| 6,063,121 A * | 5/2000 | Xavier et al. | 623/17.15 |
| 6,071,031 A * | 6/2000 | Bailey | 403/57 |
| 6,099,571 A * | 8/2000 | Knapp | 623/21.16 |
| 6,168,341 B1 * | 1/2001 | Chene et al. | 403/76 |
| 6,234,703 B1 * | 5/2001 | Bieg et al. | 403/115 |
| 6,284,000 B1 * | 9/2001 | Ege | 623/21.11 |
| 6,290,725 B1 * | 9/2001 | Weiss et al. | 623/20.12 |
| 6,352,560 B1 * | 3/2002 | Poeschmann et al. | 623/23.4 |
| 6,375,684 B1 | 4/2002 | Kriek | |
| 6,379,387 B1 * | 4/2002 | Tornier | 623/20.12 |
| 6,423,097 B2 * | 7/2002 | Rauscher | 623/21.16 |
| 6,454,808 B1 * | 9/2002 | Masada | 623/21.15 |
| 6,485,520 B1 * | 11/2002 | Hubach et al. | 623/21.13 |
| 6,607,558 B2 * | 8/2003 | Kuras | 623/17.16 |
| 6,644,671 B1 * | 11/2003 | Maughan et al. | 277/635 |
| 6,682,562 B2 * | 1/2004 | Viart et al. | 623/17.14 |
| 6,682,565 B1 * | 1/2004 | Krishnan | 623/21.16 |
| 6,699,290 B1 * | 3/2004 | Wack et al. | 623/20.12 |
| 6,716,248 B2 * | 4/2004 | Huene | 623/20.12 |
| 6,726,392 B2 * | 4/2004 | El-Haw et al. | 403/56 |
| 6,758,623 B2 * | 7/2004 | Bushey | 403/57 |
| 6,890,357 B2 * | 5/2005 | Tornier | 623/20.12 |
| 6,890,358 B2 * | 5/2005 | Ball et al. | 623/21.13 |
| 6,997,957 B2 * | 2/2006 | Huene | 623/20.11 |
| 7,140,969 B2 * | 11/2006 | Prucher | 464/134 |
| 7,179,294 B2 * | 2/2007 | Eisermann et al. | 623/17.15 |
| 7,247,170 B2 * | 7/2007 | Graham et al. | 623/20.13 |
| 7,419,507 B2 * | 9/2008 | Cook et al. | 623/20.13 |
| 7,445,399 B2 * | 11/2008 | Dunn et al. | 403/150 |
| 7,449,028 B2 * | 11/2008 | Ball | 623/20.13 |
| 7,491,239 B2 * | 2/2009 | Doubler et al. | 623/17.14 |
| 7,563,287 B2 * | 7/2009 | Guerard et al. | 623/21.13 |
| 7,604,666 B2 * | 10/2009 | Berelsman et al. | 623/20.12 |
| 7,637,955 B2 * | 12/2009 | Marik et al. | 623/17.14 |
| 7,670,077 B2 * | 3/2010 | Jan et al. | 403/90 |
| 7,827,649 B2 * | 11/2010 | Horian | 15/144.2 |
| 7,837,738 B2 * | 11/2010 | Reigstad et al. | 623/21.11 |
| 7,850,737 B2 * | 12/2010 | Morrey | 623/20.12 |
| 7,922,728 B2 * | 4/2011 | Tornier et al. | 606/87 |
| RE42,805 E * | 10/2011 | Tornier et al. | 623/20.12 |
| 8,052,755 B2 * | 11/2011 | Naidu | 623/21.12 |
| 8,062,371 B2 * | 11/2011 | de Villiers et al. | 623/17.14 |
| 8,083,190 B1 * | 12/2011 | Ma et al. | 248/181.1 |
| 8,088,168 B2 * | 1/2012 | Hassler et al. | 623/21.12 |
| 8,113,733 B2 * | 2/2012 | Bushey | 403/57 |
| 8,262,732 B2 * | 9/2012 | de Villiers et al. | 623/17.14 |
| 2001/0025199 A1 * | 9/2001 | Rauscher | 623/21.13 |
| 2003/0144739 A1 * | 7/2003 | Huene | 623/20.12 |
| 2003/0208276 A1 * | 11/2003 | Berelsman et al. | 623/20.11 |
| 2003/0208277 A1 * | 11/2003 | Weiss et al. | 623/20.12 |
| 2004/0102853 A1 * | 5/2004 | Boumann et al. | 623/21.16 |
| 2004/0186581 A1 * | 9/2004 | Huene | 623/20.12 |
| 2004/0220675 A1 * | 11/2004 | Lewis et al. | 623/20.11 |
| 2004/0243243 A1 * | 12/2004 | Tornier | 623/20.12 |
| 2006/0004462 A1 * | 1/2006 | Gupta | 623/21.13 |
| 2006/0030946 A1 * | 2/2006 | Ball et al. | 623/21.13 |
| 2006/0100712 A1 * | 5/2006 | Ball | 623/20.13 |
| 2006/0100713 A1 * | 5/2006 | Ball | 623/20.13 |
| 2007/0135919 A1 | 6/2007 | Aebi | |
| 2008/0051909 A1 * | 2/2008 | Wolfe et al. | 623/21.12 |
| 2009/0041534 A1 * | 2/2009 | Bushey | 403/57 |
| 2009/0312840 A1 * | 12/2009 | Morrey | 623/20.11 |
| 2010/0179661 A1 * | 7/2010 | Berelsman et al. | 623/20.12 |
| 2010/0222887 A1 * | 9/2010 | Katrana et al. | 623/20.11 |
| 2011/0125274 A1 * | 5/2011 | Bartel et al. | 623/20.11 |
| 2011/0153024 A1 * | 6/2011 | Wagner et al. | 623/20.12 |
| 2012/0053697 A1 * | 3/2012 | Palmer et al. | 623/20.12 |

FOREIGN PATENT DOCUMENTS

| | | |
|---|---|---|
| DE | 10354601 B3 | 6/2005 |
| WO | 97/26846 A1 | 7/1997 |
| WO | 2004054477 A | 7/2004 |

* cited by examiner

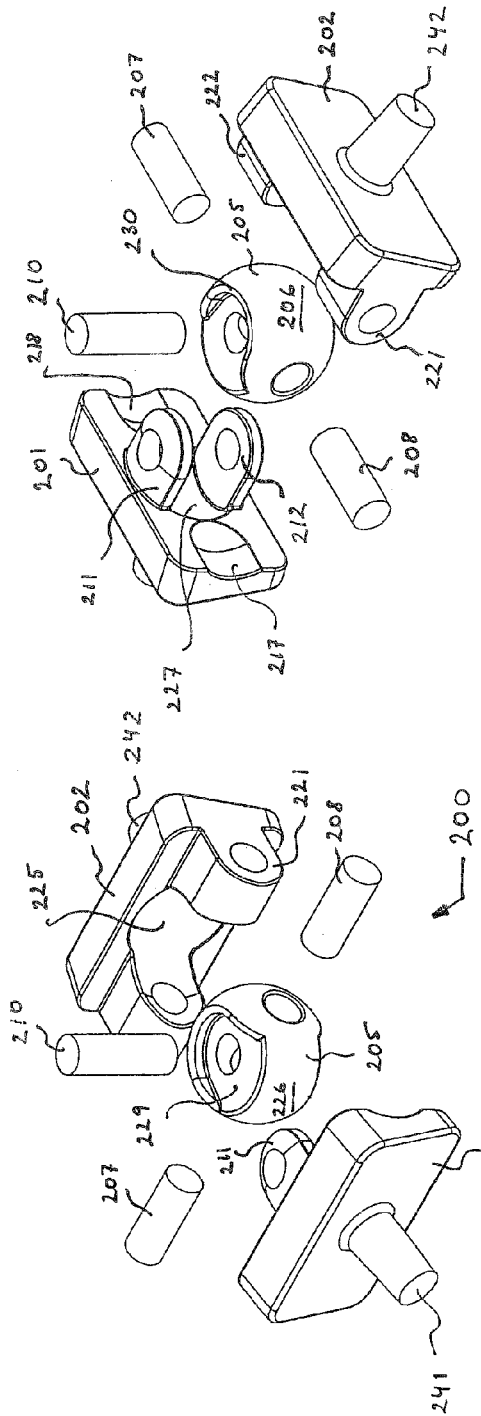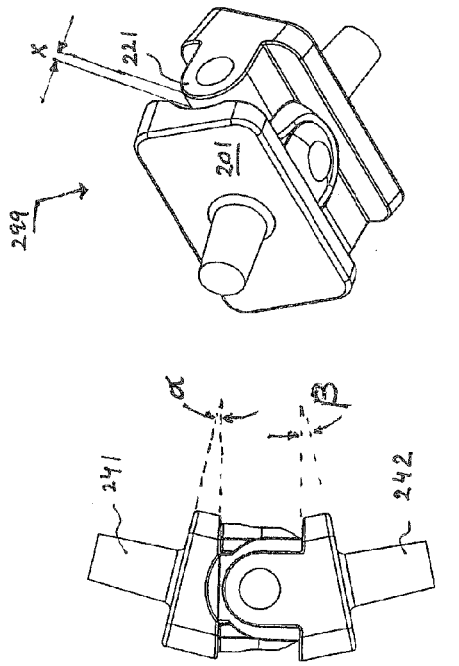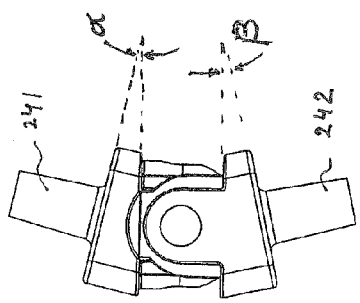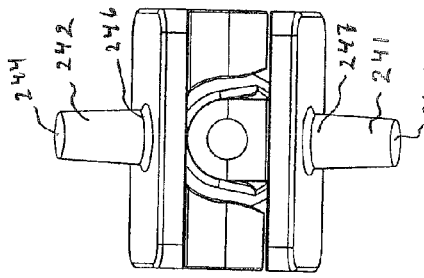

ARTIFICIAL JOINT

RELATED APPLICATIONS

This is a U.S. national phase application of PCT/EP2008/0065016, filed Nov. 5, 2008, which claims priority to European Application No. 07120198.2, filed Nov. 7, 2007, both of which are incorporated herein by reference.

FIELD OF THE INVENTION

The present invention relates to an artificial joint for implantation into humans and animals having the need for replacing a malfunctioning or hurting joint. The artificial joint comprises two fixing elements to be connected to adjoining implanted screws fixed to adjoining bone parts, which fixing elements are arranged to form an artificial joint together with zero or more additional elements.

BACKGROUND OF THE INVENTION

Several diseases cause destruction of joints, resulting in chronic pain and impaired flexibility and agility. The problem is most pronounced in patients who suffer from chronic rheumatoid arthritis, but is also pronounced in, for instance, osteoarthritis (wear of cartilage) and in articular cartilage injuries after fractures and bacterial infections. In many of these cases the diseased and injured joint is replaced by an artificial joint structure.

However, experience has shown that too great an ambition to completely imitate the function of a normal joint in many cases results in failure. The artificial joint will easily be too complicated. For a rheumatic who has no joint function at all in, for instance, in hands, it is not necessary to aim at regaining a fully normal joint function via prosthetic operation. The aim should instead be to obtain a painless joint with a stability and a certain amount of movability, which makes the hand usable. Thus, the aim of the joint structure must always be related to the patient's needs.

The main difficulties when constructing artificial joints in e.g. the hand have been (1) to provide an artificial joint with satisfactory properties and (2) to fix the artificial joint to adjoining bones in a satisfactory manner.

WO 97/26846 discloses a prosthetic device comprising a joint body which includes one or more substantially helical spring means arranged between two fixing elements which are adapted to be connected to adjoining bone parts. This prosthetic device obviates many of the drawbacks that are associated with other known artificial prosthetic devices for joints that are available today. However the springs of this system is always susceptible to wear and friction, especially when forces are applied. Also the endurance of the springs is essential for the function of the prosthetic device.

SUMMARY OF THE INVENTION

The general object of the present invention is to provide an artificial joint that obviates the drawbacks that are associated with artificial prosthetic devices for joints that are available today. More particularly, the object of the present invention is to provide an artificial joint suitable for finger joints. The invention also has the property to be constrained, which differs from many of the existing artificial joints. In the context of the present application the term "constrained" refers to the quality of a plurality of parts being held together, in contrast to a plurality of parts only staying together because external forces or external structures makes them stay together. Some existing artificial joints rely on endogenous tissues, such as tendons and ligaments, to cope with traction forces applied to the body structure comprising the artificial joint.

The joint implant system consists of two bone anchored titanium screws which is permanently fixed to the bones. The artificial joint has two coned pins which fit into the head of the titanium screws. The device is pre-flexed in the range of 15 to 25 degrees in order to achieve a normal resting position of the hand.

One factor of importance is the endurance of the artificial joint. Since the available space for a finger joint is limited, the artificial joint has to be relatively strong for its size. It is also an objective of the invention to be able to provide an artificial joint particularly suitable for the metacarpophalangeal (MCP) joint, that is the joint between the metacarpus and the first phalangea of a finger. A special demand on a replacement MCP joint is that it in addition to its hinge joint function should be able to provide a certain degree of movement in a direction perpendicular to the normal bending of the MCP joint when a subject bends his or her fingers. Durability and a long functional life time of any element of the artificial are also of great importance.

A certain activity of a subject that puts lots of strain on the meta-carpophalangeal joint is the activity of rising from a chair by supporting a fist towards a table or towards an armrest of the chair. Such an activity applies a lot of pressure forces on the artificial joint, necessitating for large contact surfaces. Another activity which puts strain on the joints is when the person carries an item, such as a bag, which applies traction forces on the artificial joint, and/or on remaining endogenous tissues. The forces applied onto the artificial finger joint are in the order of 100 Newton. The present invention alleviates this problem by providing retaining structures.

Another factor of concern is the adverse tissue reactions that may be caused by undesired tissue ingrowth between elements of the artificial joint, which can lead to inflammation and stiffening of the joint.

In order to fulfill the above objects, there is provided a prosthetic device for joints usable for implantation in humans and animals, as an artificial joint according to claim 1.

The prosthetic device is preferably intended for reconstruction of the metacarpophalangeal joints (MCP), the proximal interphalangeal joints (PIP) or the distal interphalangeal joints (DIP) in humans, i.e., the invention provides an artificial metacarpophalangeal joint, but also an artificial proximal interphalangeal joint, and an artificial distal interphalangeal joint.

The inventors have a number of general ideas for providing the artificial joint with both good flexibility and high stress resistance. One of them is that a spherical ball joint provides flexibility to bend the artificial joint in multiple directions. Another is that a spherical ball confers compressional force resistance, by designing the artificial joint such that an unbroken chain of mechanical contact transfers compression forces via proportionally large contact surfaces.

One of the objectives of the present invention is to provide an artificial finger joint that is constrained. With a constrained joint the risk for luxation is minimized. Another objective is to provide a joint that can have a large freedom of movement in the flexion/extension direction of a normal finger. Furthermore, the invention makes it possible to limit the movement sidewise to the same range as a normal finger joint. This means that the sidewise movement can be made different for the MCP and the PIP joints. The artificial joint according to this invention distributes the applied forces, positive or negative, to relatively large surfaces compared to the size of the joint. With the preferred choice of material for the joint it can withstand large stresses. The endurance of the artificial joint with the preferred material choice is long since the wear is minimized. The finger joint is preassembled which makes it is easy to apply in position and makes it easily interchangeable.

Thus, according to a first aspect there is provided an artificial joint comprising a first base element and a second base element; for being attached to bone members of a patient, between which bone members the artificial joint is to be arranged where the artificial joint comprises:
- a joint body having at least one convex curved surface;
- a concave curved surface arranged at one of the base elements to make sliding contact with the convex curved surface of the joint body;
- one or more retaining members and stub axles arranged to keep the artificial joint constrained.

According to a second aspect there is provided the artificial joint where the convex curved surface of the joint body is a convex spherical surface and where a corresponding concave curved surface of a base element is a concave spherical surface.

According to a third aspect there is provided the artificial joint according to above where the convex curved surface of the joint body is a convex cylindrical surface and in that the concave curved surface is a concave cylindrical surface.

According to a fourth aspect there is provided the artificial joint where the one or more retaining members are arranged to confine the joint body in a position where the concave curved surface arranged at one of the base elements is able to make sliding contact with the convex curved surface of the joint body.

According to a fifth aspect there is provided the artificial joint where the first base element comprises an upper retaining member, and a lower retaining member arranged to hold the joint body between them.

According to a sixth aspect there is provided the artificial joint where the second base element comprises a left retaining member, and a right retaining member arranged to hold the joint body between them.

According to a seventh aspect there is provided the artificial joint where the first and second base elements are arranged so close together that a side-to-side movement may be more or less prevented by the left (221, 321) or right retaining member of the second element coming into contact with the first base element.

According to a eighth aspect there is provided the artificial joint where the first base element is provided with a left recess arranged opposite left retaining member.

According to a ninth aspect there is provided the artificial joint where the first base element is provided with a right recess opposite the right retaining member.

According to a tenth aspect there is provided the artificial joint where a cylindrical concave surface is provided in each retaining member and where cylindrical bores are arranged in the ball member to enable arrangement of a vertical pin passing through the upper retaining member, the joint body, and the lower retaining member, to secure the joint body in position, and to allow for a certain articulation side to side.

According to an eleventh aspect there is provided the artificial joint where the upper and lower retaining members are manufactured integral with the first base plate.

According to a twelfth aspect there is provided the artificial joint where each of respective fixing members for fixing the base elements to adjoining bone, projects away from their corresponding base plate at an angle of 7 to 13 degrees in relationship to the longitudinal direction of the joint.

According to a thirteenth aspect there is provided the artificial joint where the joint is intended for reconstruction of the metacarpophalangeal joints (MCP), the proximal interphalangeal joints (PIP) or the distal interphalangeal joints (DIP).

According to a fourteenth aspect there is provided the artificial joint where the base elements are made of titanium and where the curved convex surface of the joint body is made of a polymer material.

According to a fifteenth aspect there is provided the artificial joint where the joint comprises:
- a joint body comprising a first convex curved surface, and a second convex curved surface, different from any curved surface of any stub axles or retaining members;
- a first and a second base element arranged to hold the joint body between them, where the second base element comprises a first concave curved surface, different from any curved surface of any stub axles or retaining means, arranged to make sliding contact with first convex curved surface of the joint body;
- the first base element comprising a second concave curved surface, different from any curved surface of any stub axles or retaining members, arranged to make sliding contact with second convex curved surface of the joint body;
- one or more retaining members arranged at the base elements facing the joint body and stub axles arranged at the joint body, arranged to keep the artificial joint constrained.

According to a sixteenth aspect there is provided the artificial joint where the joint body comprises an upper shelf and corresponding upper shelf edging and lower shelf and corresponding lower shelf edging defining the upper and lower shelves, respectively, where said shelves and retaining members are arranged such that said shelves make contact to upper and lower retaining members to allow for transmission of compression forces.

According to a seventeenth aspect there is provided the artificial joint where the shelf edging are arranged to allow for limited angular movement of the base element relative to the joint body.

DESCRIPTION OF THE DRAWINGS

The present invention will be described in more detail below, with the aid of a number of preferred embodiments and with reference to the accompanying drawings, of which:

FIG. 2a illustrates, in a perspective view from distal upper left, an exploded artificial joint according to a first embodiment of the present invention.

FIG. 2b illustrates, in a perspective view from proximal upper left, the artificial joint of FIG. 2a.

FIG. 2c illustrates, in a view from beneath, the artificial joint of FIG. 2a, in an assembled, non-exploded manner.

FIG. 2d illustrates, in a perspective view from the side, the artificial joint of FIG. 2c.

FIG. 2e illustrates, in an oblique perspective view, the artificial joint of FIG. 2c.

FIG. 3b illustrates, in a perspective view from proximal upper left, the artificial joint of FIG. 3a.

DETAILED DESCRIPTION OF THE EMBODIMENTS

By the expression "longitudinal direction of the joint body", which is used below throughout, is meant the axial direction in which the joint and its adjoining bone parts extend in a stretched condition.

Figure 1:
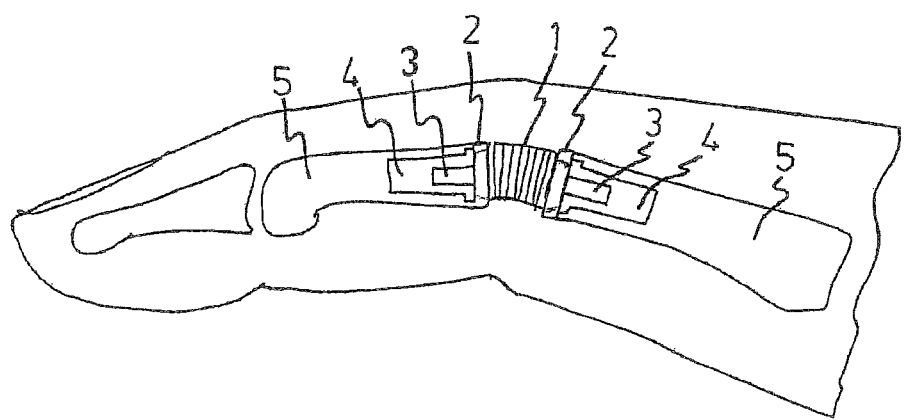
FIG. 1a illustrates a finger having one of its joints replaced by an prosthetic device according to prior art.
Figure 3E:
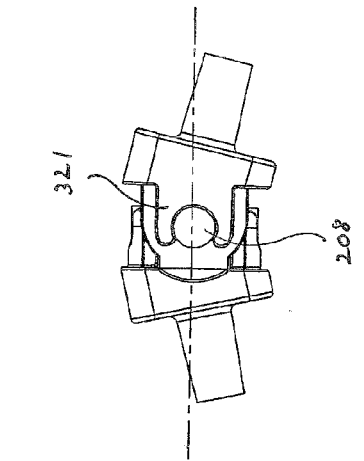
FIG. 3e illustrates, in a view from the side, the artificial joint of FIG. 3c.
Figure 3B:
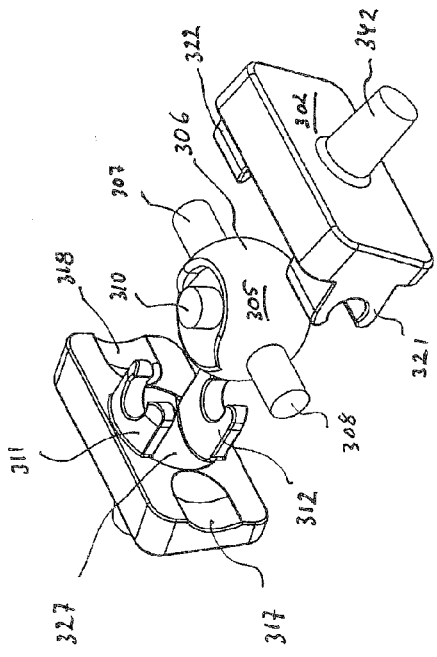
Figure 3D:
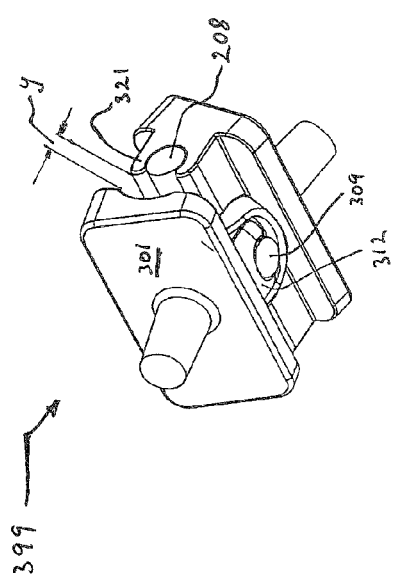
FIG. 3d illustrates, in an oblique perspective view, the artificial joint of FIG. 3c.
Figure 3A:
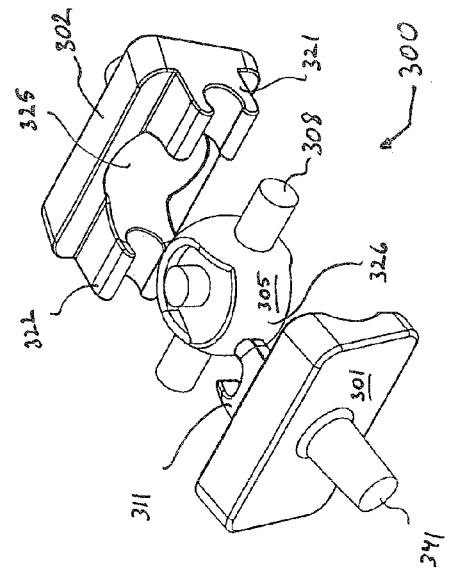
FIG. 3a illustrates, in a perspective view from distal upper left, an exploded artificial joint according to a second embodiment of the present invention.
Figure 3C:
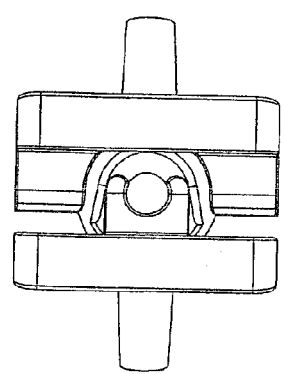
FIG. 3c illustrates, in a view from above, the artificial joint of FIG. 3a, in an assembled, non-exploded manner.

FIG. 1 is a side view of an artificial joint according to prior art. The artificial joint is replacing an intermediate finger joint. The joint having a joint body of two parallel helical cylindrical springs 1 arranged in a plane perpendicular to the plane of bending of the joint body and the finger. These two springs 1 are, at each end, via a base plate 2 and a fixing member 3 fixed to anchoring means, titanium screws, 4 in adjoining bone parts 5.

FIG. 2a illustrates, in a perspective view from distal upper left, an exploded artificial joint 200 according to a first embodiment of the present invention. The artificial joint 200 comprises a first base element in the form of a first base plate 201, and a second base element in the form of a second base plate 202, and a ball member 205 designed to be arranged between the first base plate 201 and the second base plate 202. The base plates are preferably rectangular in shape.

The first base plate 201 is provided with an upper yoke member 211, and a lower yoke member 212 arranged to hold the ball member 205 between them. The upper and lower yoke members are preferably manufactured integral with the base plate. A holding arrangement for the ball member is provided. This may be in the form of bores and pin(s) or just by arranging stub axles at the ball member. In the present embodiment a bore is provided in each yoke member and in the ball member to enable arrangement of a vertical pin passing through the upper yoke member 211, the ball member 205, and the lower yoke member 212, to secure the ball member 205 in position, and to allow for articulation.

The second base plate 202 is provided with a left yoke member 221, and a right yoke member 222 arranged to hold the ball member 205 between them. The left and right yoke members are preferably manufactured integral with the second base plate 202. A bore is provided in each yoke member and in the ball member 205 to enable arrangement of two pins 207, 208. A left pin 208 passes through a bore in the left yoke member 221, and into a bore in a left portion of the ball member 205. A right pin 207 passes through a bore in the right yoke member 222, and into a bore in a right portion of the ball member 205, to secure the ball member 205 in position, and to allow for articulation.

The ball member 205 is preferably provided with upper shelf 229, and upper shelf edging 230 and lower shelf and lower shelf edging (non to be seen in FIG. 2a or 2b) to enable pressure forces in a direction compressing the artificial joint, to be distributed from the upper and/or lower yoke member via the edging and the ball over to the second base plate, and eventually to a bone part. The design of the upper shelf, 229 and the lower shelf (not shown) enables movement in sidewise direction. The upper and lower shelves have an area, limited by shelf edging 230 slightly larger than the upper and lower yoke members, to allow for restricted pivoting of the yoke members around vertical pin 210.

The left 221 and right 222 yoke members of the second base plate 202 are on top rounded to make contact with corresponding concave recesses 217, 218. This is further advantageous to distribute compression forces and to decrease wear, decrease probability of joint breaking, and increase life span of joint 200.

A second embodiment of an artificial joint according to the present invention is shown in FIGS. 3a to 3e. The artificial joint 300 comprises a first base element 301 with upper 311 and lower 312 retaining members, a second base element 302 with left 321 and right 322 retainer members and a cross pin member 305. The cross pin member being manufactured of a high strength material to cope with the proportionally high stressing forces that arise due to the relative small size of the joint and the cross pin member 305. The cross pin member 305 may comprise a cross pin 307, 308, 309, 310 permanently fixed into a spherical body 305, or may comprise a cross pin manufactured integral with a spherical central portion.

Each of the retaining members 311, 312, 321, 322 have an elongated opening to allow the pins 307, 308, 309, 310 of the cross pin member 305 to be pressed into the retaining members. Retaining members comprises cylindrical surface to make contact to pins to enable a pivoting relationship between cross pin member 305 and retaining members 311, 312, 321, 322. To facilitate the attachment of the pins during assembly, the base element with its retaining members may be heated.

In alternative embodiments the convex spherical surface of the joint body 205 may be a convex cylindrical surface, and the concave spherical surface of the base element 202 may be concave cylindrical surface adapted to make sliding contact to the convex cylindrical surface. This is possible because the pins restricts the movement between the first base element and the joint body to a pivoting movement in one direction only. Correspondingly, the pins restricts the movement between the second base element and the joint body to a pivoting movement also in one direction only, however in a direction principally perpendicular to the pivoting direction between the joint body and the first base element.

The joint body in a further embodiment of an artificial joint according to the present invention comprises a body having a first and a second convex curved surface for contacting corresponding first and second concave curved surfaces arranged at the base elements. The joint body is further provided with a first and a second pair of shaft pivots, or axle bars, or stub axles, or pins or the like for providing constraining means for the joint body. The first and second pair of stub axles are arranged principally perpendicular in relation to each other to provide for pivotal movement in two independent directions. The first pair of stub axles and the first convex surface are arranged to have a first common axis of rotation. The second pair of stub axles and the second convex surface are arranged to have a second common axis of rotation, different from the first common axis of rotation.

In all the described embodiments the joint body is relatively large in size occupying approximately one third of largest cross sectional dimension of a base element or more. The larger the joint body the larger the surfaces for conveying compression forces can be made, resulting in less strain on the material and less wear. On the other hand, the available space to arrange structures to cope with traction forces becomes less. One of the advantages of the invention is its ability to, in the very same device use available space efficiently to handle both compression and traction forces. The relative size of the pins compared to the joint body affects the ability to deal with traction forces of the same magnitude as the compression forces. The larger diameter and length of a pin the larger fraction forces may be conveyed. However too large diameter and/or length would interfere with the angular range of movement of the artificial joint. A suitable relationship between joint body diameter and pin diameter is between six to one and three to one (6:1 to 3:1).

In a preferred embodiment the joint body is ball shaped and has a diameter of 6 millimeters. The stub axles have a diameter of 1.75 millimeters. Simulations conducted by the inventors, using a simulated fraction force of 100 Newton, show good performance regarding strength and durability.

Connection to Bone Parts

The two base plates 201, 202 are adapted to be connected, although this is not part of the invention, via fixing members 241, 242, to fixed anchoring means 4, such as titanium screws, inserted in adjoining bone parts 5.

Several conventional, suitable methods for attachment are available. An established method means, as mentioned above, that the fixing members 241, 242 in the form of shafts, which protrude from the base plates 201, 202, are inserted in longitudinal channels in the longitudinal direction of the anchoring means 4. The anchoring means 4 can be made of ceramic material, titanium or some other material having suitable biological and mechanical properties.

Material Considerations

As mentioned above, the base plates 201, 202 in the artificial joint according to the present invention can be made of any suitable biocompatible material having sufficient strength and durability.

In a preferred embodiment the first and second base elements are manufactured in titanium. Surfaces that are subjected to frictional sliding contact with each other, such as the convex spherical surface 206 of ball member 205 and a concave spherical surface 225 of second base plate 202 are preferably arranged such that a metal surface makes contact to a polymer surface to achieve a small friction coefficient. Metal material is preferably titanium, stainless steel, or cobalt alloys made for medical implants. Polymer material is preferably ultra high molecular weight polyethylene (UHMW). In another preferred embodiment the polymer material is ChronoFlex AL polyurethane (PolyMedica). In a further embodiment the polymer is a low-density polyethylene/ethylene-vinyl acetate copolymer LDPE/EVA blend.

In a further embodiment one or both of the surfaces that are subjected to frictional sliding contact with each other is made of a ceramic material.

Joint Range of Motion

In the preferred design, the joint is pre-flexed in a range of 15 to 25 degrees to obtain a relaxed resting position. The pre-flexed range is determined by the angles α and β in FIG. 2d. The range of motion of the joint can be controlled upon design by adding or removing material on critical positions of the base plates. Two such critical positions are the recesses 217, 218 of the first base plate. By making the recess 217 deeper, the left yoke member 221 can move deeper and thereby the range of motion of the joint increases to the left, as seen from the second base plate. This procedure can be applied on both sides and thereby determines the sidewise movement of the finger. The normal longitudinal down movement angle of the finger is determined by a bottom portion of the base plates 201 and 202 to reach 90 degrees. The possible movement upwards is restricted by upper portions of the base plates 201, 202 to correspond to a normal joint.

Resting Position

The surface of the base plate which is directed to the fixing member 241 and 242 can be angled in relation to the longitudinal direction of the artificial joint considered as a whole, to achieve an advantageous position of the joint to better withstand external forces. Alternatively, as is best seen in FIG. 2d, an angle alfa (α) between a surface of the first base plate facing towards a joint centre, and a surface facing towards the fixing member 241, can be varied to achieve an advantageous position of the joint to better withstand external forces in a bending position of the joint where such forces are particularly troublesome. The same is valid for fixing member 242 and corresponding angle beta (β).

Capsule

After implantation of an artificial joint according to the present invention, a thin capsule consisting of a soft tissue automatically forms, as mentioned above, around the artificial joint. If necessary, the joint may be provided with an artificial outer capsule for the purpose of minimizing undesired tissue in-growth in the system. Such a capsule may consist of a thin membrane of a woven or homogeneously deformable material with suitable biological and mechanical properties. The membrane can be resorbed or not.

The forming of an outer biological membrane around the joint is facilitated by the act of surrounding the joint with a tube of a biocompatible, optionally resorbable material. Said tube, however, does not constitute a supporting body for the prosthetic device for joints. In this way, a biological capsule forms automatically around the joint after implantation.

Applications

The present invention is particularly applicable to reconstruction of the knuckle joints (MCP joints) and the intermediate and outer joints of the fingers (PIP and DIP joints).

The invention can also be used in the wrist, or in the thumb base, or for alleviating osteoarthrosis by bone replacement for the trapezoid bone or as artificial joint between the first metacarpal bone and the trapezoid bone and/or between the trapezoid and the navicular bone. The invention can also be used as bone replacement for intervertebral discs or individual vertebrae in the spinal column. The present invention is, of course, also applicable to other similar joint and bone systems in the body, also where replacement structures are now rare, but which may be of interest in future, for instance in the joints of the foot.

By selecting a suitable size and configuration of elements of the artificial joint the contour of the normal articular head can be imitated in a cosmetically advantageous fashion.

The dimensions of the elements of the artificial joint are not restricted, but may of course vary depending on the dimensions of the joint or bone part that is to be replaced in the human or animal at issue. For the MCP joint the size is preferable 6-8 mm in length, 10-15 mm width and a height of 5-8 mm. The sidewise deflexion is 5-10 degrees in each direction. For the PIP the preferable size is slightly less and the sidewise deflexion is less than 5 degrees.

The invention claimed is:

1. An artificial joint comprising a first base element and a second base element; for being attached to bone members of a patient, between which bone members the artificial joint is to be arranged, wherein the artificial joint comprises:
   a joint body having a first convex curved surface, and a second convex curved surface;
   wherein the second base element comprises a first concave curved surface arranged to make sliding contact with the first convex curved surface of the joint body;
   wherein the first base element comprises a second concave curved surface arranged to make sliding contact with the second convex curved surface of the joint body; and
   one or more retaining members and stub axles arranged to keep the artificial joint constrained.

2. The artificial joint according to claim 1 where the convex curved surfaces of the joint body are convex spherical surfaces and in that the concave curved surfaces are concave spherical surfaces.

3. The artificial joint according to claim 1 where the convex curved surfaces of the joint body are convex cylindrical surfaces and in that the concave curved surfaces are concave cylindrical surfaces.

4. The artificial joint according to claim 1 where the one or more retaining members are arranged to confine the joint body in a position where the concave curved surfaces arranged at the base elements are able to make sliding contact with the convex curved surfaces of the joint body.

5. The artificial joint according to claim 1, where the first base element comprises an upper retaining member, and a lower retaining member arranged to hold the joint body between them.

6. The artificial joint according to claim 5 where a cylindrical concave surface is provided in each retaining member and where cylindrical bores are arranged in the joint body to enable arrangement of a vertical pin passing through the upper retaining member, the joint body, and the lower retaining member, to secure the joint body in position, and to allow for a certain articulation side to side.

7. The artificial joint according to claim 5 where the upper and lower retaining members are manufactured integral with the first base plate.

8. The artificial joint according to claim 5 where the joint body comprises an upper shelf and corresponding upper shelf edging and lower shelf and corresponding lower shelf edging defining the upper and lower shelves, respectively, where said shelves and retaining members are arranged such that said shelves make contact to upper and lower retaining members to allow for transmission of compression forces.

9. The artificial joint according to claim 8, where the shelf edgings are arranged to allow for limited angular movement of the base element relative to the joint body.

10. The artificial joint according to claim 1, where the second base element comprises a left retaining member, and a right retaining member arranged to hold the joint body between them.

11. The artificial joint according to claim 1 where the first and second base elements are arranged so close together that a side-to-side movement may be more or less prevented by a retaining member of the second element coming into contact with the first base element.

12. The artificial joint according to claim 11 where the first base element is provided with a recess arranged opposite a left retaining member of the second base element.

13. The artificial joint according to claim 12 where the first base element is provided with a recess arranged opposite a right retaining member of the second base element.

14. The artificial joint according to claim 1, wherein each base element comprises a fixing member configured to fix the respective base member to an adjoining bone member, wherein each fixing member projects away from its corresponding base member at an angle of 7 to 13 degrees in relationship to a longitudinal direction of the joint.

15. The artificial joint according to claim 1 where the joint is intended for reconstruction of the metacarpophalangeal joints (MCP), the proximal interphalangeal joints (PIP) or the distal interphalangeal joints (DIP).

16. The artificial joint according to claim 1 where the base elements are made of titanium and where the curved convex surface of the joint body is made of a polymer material.

17. An artificial joint comprising:
 a first base element and a second base element configured to be attached to bone members of a patient between which bone members the artificial joint is to be arranged;
 a joint body having at least one convex curved surface;
 a concave curved surface arranged at one of the base elements to make sliding contact with the convex curved surface of the joint body; and
 one or more retaining members and stub axles arranged to keep the artificial joint constrained
 wherein the first base element comprises an upper retaining member, and a lower retaining member arranged to hold the joint body between them;
 wherein the joint body comprises an upper shelf and corresponding upper shelf edging and lower shelf and corresponding lower shelf edging defining the upper and lower shelves, respectively, where said shelves and retaining members are arranged such that said shelves make contact to upper and lower retaining members to allow for transmission of compression forces.

18. The artificial joint according to claim 17 wherein the shelf edgings are arranged to allow for limited angular movement of the base element relative to the joint body.

* * * * *